United States Patent [19]

Doyle et al.

[11] Patent Number: 4,784,488
[45] Date of Patent: Nov. 15, 1988

[54] MODULAR RADIATION TRANSMISSION APPARATUS FOR SPECTROMETERS

[75] Inventors: Walter M. Doyle, Laguna Beach; Norman S. Hughes, San Clemente, both of Calif.

[73] Assignee: Laser Precision Corporation, Irvine, Calif.

[21] Appl. No.: 900,730

[22] Filed: Aug. 27, 1986

[51] Int. Cl.$^4$ .................... G01B 9/02; G01N 21/01
[52] U.S. Cl. .................... 356/346; 356/244; 356/73
[58] Field of Search .................... 356/73, 244, 346

[56] References Cited

U.S. PATENT DOCUMENTS

| | | | |
|---|---|---|---|
| 3,687,519 | 8/1972 | Mapes | 356/73 |
| 3,958,882 | 5/1976 | Gast | 356/73 |
| 4,484,817 | 11/1984 | Nobuto et al. | 356/414 |

Primary Examiner—Davis L. Willis
Assistant Examiner—S. A. Turner
Attorney, Agent, or Firm—Thomas J. Plante

[57] ABSTRACT

A modular spectrometer system is disclosed which includes various types of standard building blocks which permit: (a) a multiple accessory system in which experiments can be readily switched from one accessory to another; and (b) easy and cost effective revision of the multiple accessory system as desired. Optical switch components are provided which facilitate steering and switching of the radiation paths, and which are capable of being assembled from standard parts. Modular connecting tubes and interface elements are provided to interconnect components in the system. Component substitutions and position adjustments may be readily accomplished without loss of alignment in the system.

21 Claims, 9 Drawing Sheets

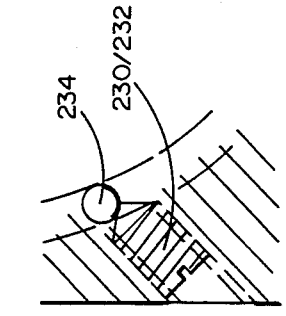
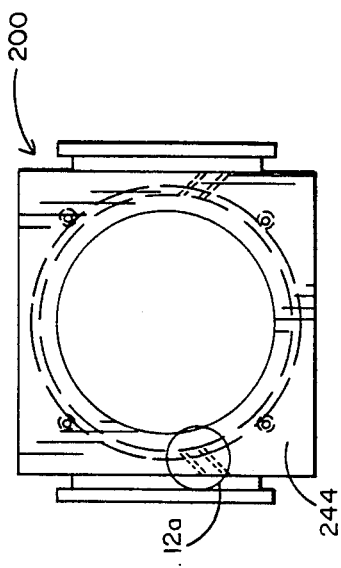
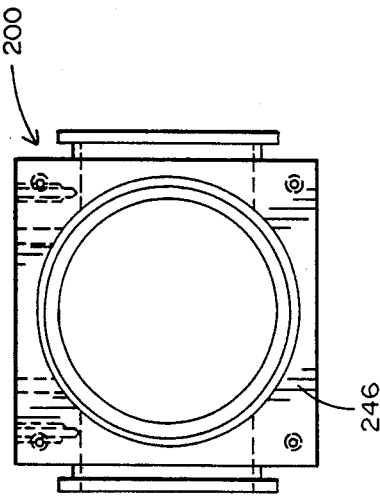
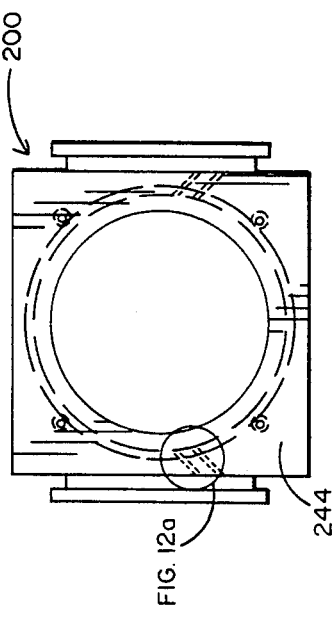
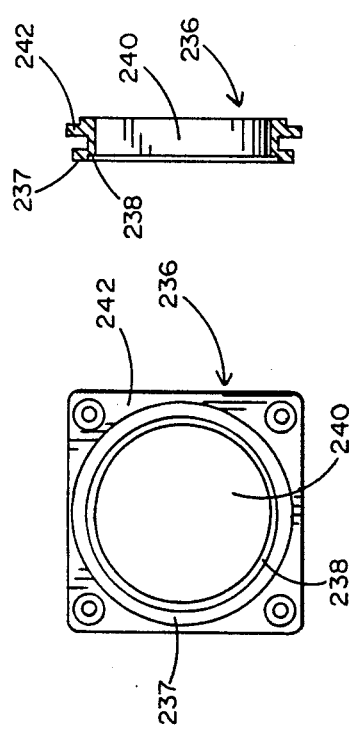
FIG. 12a
FIG. 12
FIG. 14
FIG. 11
FIG. 13
FIG. 10

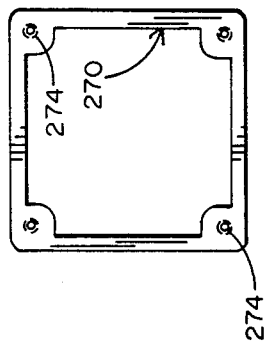
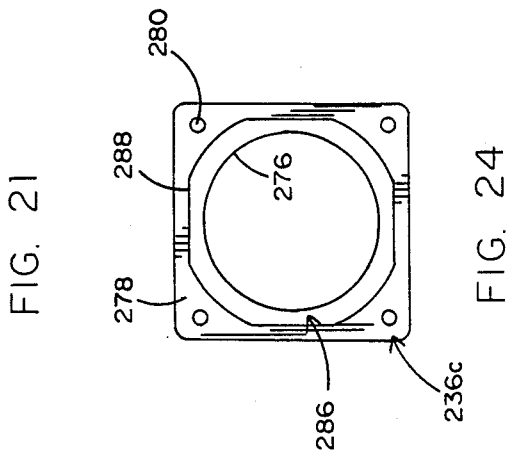
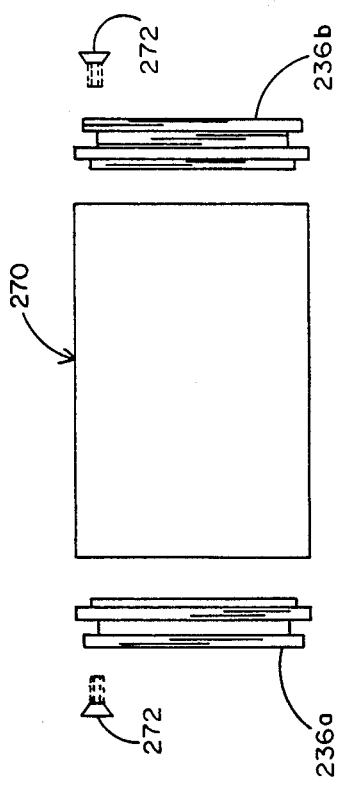
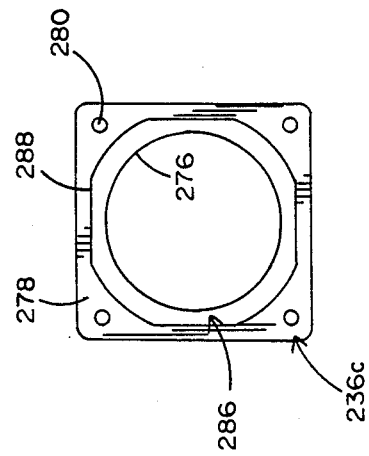
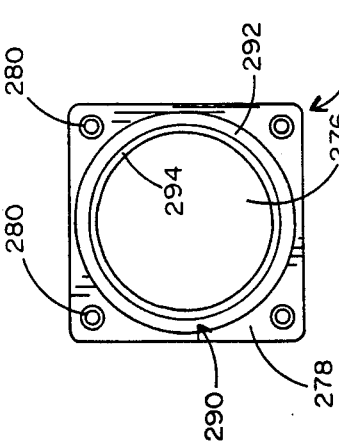
FIG. 21
FIG. 24
FIG. 20
FIG. 22
FIG. 23

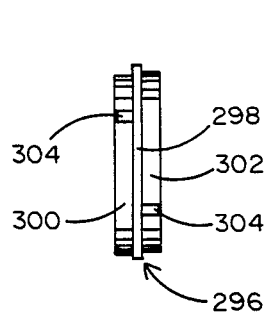
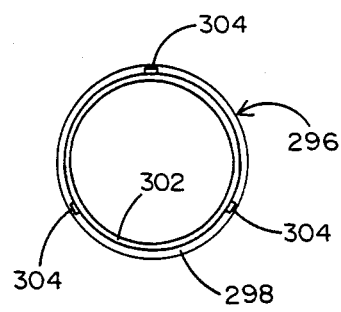
FIG. 25  FIG. 26
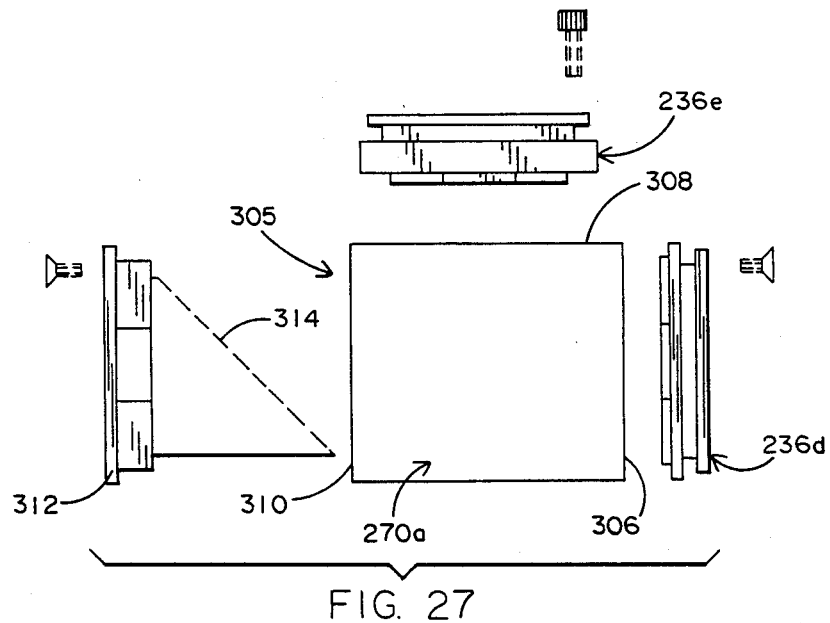
FIG. 27

MODULAR RADIATION TRANSMISSION APPARATUS FOR SPECTROMETERS

BACKGROUND OF THE INVENTION

This invention relates to radiation transmission systems which permit radiation, particularly infrared (IR) radiation, to be used in conveying information, such as spectral scanning information obtained by means of Fourier Transform spectroscopy, over relatively long distances and to various alternatively available accessory devices, or sample chambers.

In a recently filed application of one of the present inventors (Ser. No. 895,211, filed Aug. 11, 1986) a multi-unit spectrometer system is disclosed which permits a plurality of accessory units to be simultaneously connected to a single interferometer/detector unit.

The key concept of that system is the combining of confocal and collimated optical segments in an appropriate way to substantially eliminate vignetting (i.e., the loss of energy due to beam growth and the resultant loss of throughput). The use of confocal segments provides pairs of conjugate images, i.e., images in which all of the same rays are present in a matched relationship with respect to angle and location. By the proper arrangement of the optical elements in the system, the limiting aperture of the system can be reimaged at appropriate points in the system. As a result, the inherent spread of the beam is minimized, allowing the maximum possible signal to reach the detector.

SUMMARY OF THE INVENTION

The present invention provides a plurality of modular components which are used as "building blocks" in putting together radiation-transmitting systems of the type disclosed in Ser. No. 895,211.

The optical elements within each modular component are accurately aligned with respect to flanges which are used to interface with the other components. Hence, when components in the system are changed, their flange and clamp assemblies cause automatic centering and aligning of the optical elements.

Modular units of particular importance are those which provide for "switchability", permitting the operator to readily move reflecting optical elements between predetermined positions, thereby changing the direction and/or shape of the radiation in the system. Thus, a substantial number of alternative sample compartments, or modules, may be maintained in place for almost instantaneous selection.

Because the components provided by the present invention are modular, they permit the system to be changed as desired. In other words, the switchability provides the versatility of having a number of interconnected units which give the convenience of ready access, while the modularity permits easy and time-saving re-structuring of the accessory combination included in the system.

BRIEF DESCRIPTION OF THE DRAWINGS

FIGS. 10 and 11 are end and cross-section views, respectively, of an interface element used as a modular connecting member between adjacent units of the system;

FIGS. 12 and 13 are vertical elevations of the left and right ends, respectively, of the body of a modular optical switch; and FIG. 12a is a closeup of the positioning means which limits rotation of the rotary mirror mount in the switch body;

FIG. 14 is an elevation of the switch body cover;

FIGS. 20 and 21 are, respectively, an exploded view of a connecting tube assembly, and an end view of the connecting tube;

FIGS. 22, 23 and 24 are, respectively, a crosssection, and two end views of a modular interface element;

FIGS. 25 and 26 are side and end views, respectively, of a centering ring used to align two connecting elements in the system;

FIG. 27 is an exploded view showing a corner tube assembly; and

DETAILED DESCRIPTION OF SPECIFIC EMBODIMENTS

Figure 1:
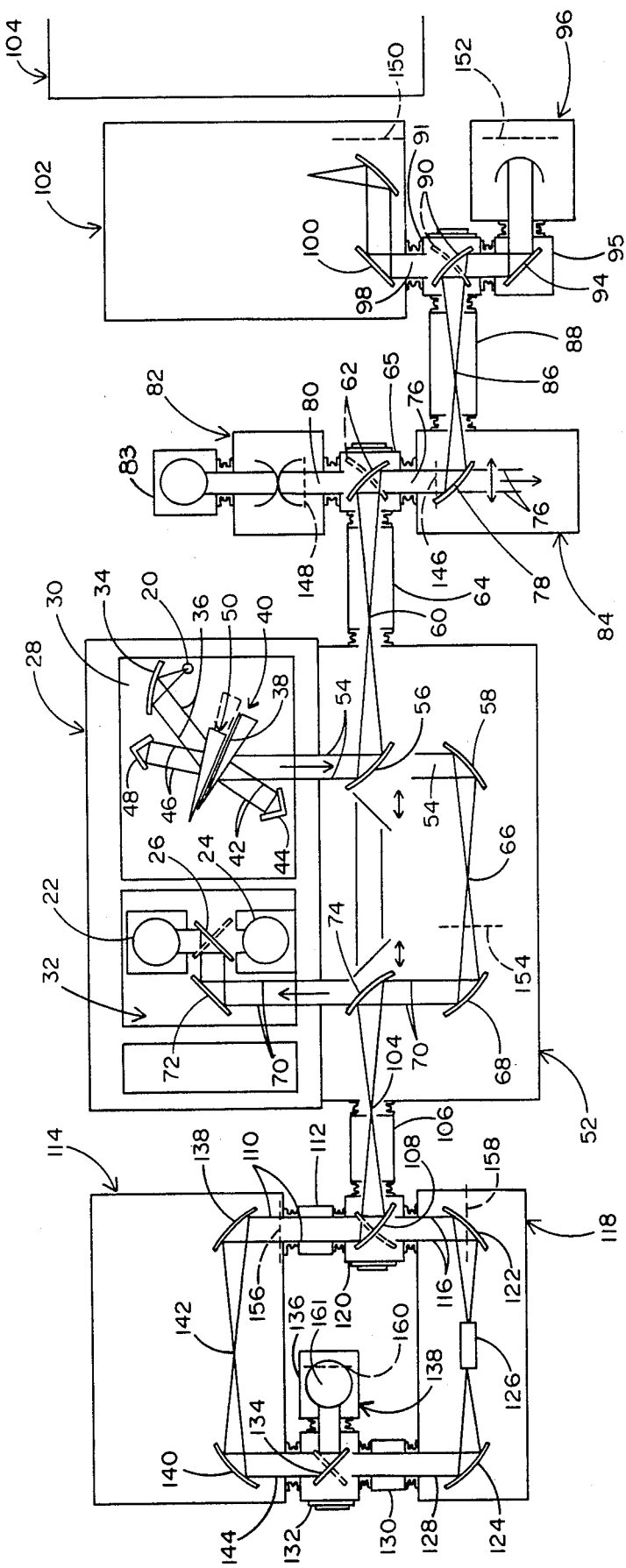
FIG. 1, which is identical to FIG. 1 of Ser. No. 895,211, is a diagrammatic showing of a comprehensive sampling system illustrating the types of modular devices and connections provided by the present invention.

In order to provide a rapid understanding of the advantages of the present invention, FIG. 1 shows a reasonably complex example of a multi-option configuration of an interferometer spectrometer system. This is only one of the virtually limitless variety of sampling systems that can be configured for use with a basic spectrometer.

In FIG. 1, the interferometer spectrometer system shown is one marketed by the assignee of this application. The inventive concepts are not, however, limited to that type of system.

The radiation in the system begins with a source 20 and ends with a detector. In the illustrated system, there are two detectors internal to the spectrometer, indicated by numerals 22 and 24. Other detectors are associated with various accessories, or peripherals, in the system. Detectors 22 and 24 have different characteristics, and are selected for separate use by moving a flat mirror 26 between its solid line and dashed line positions.

In FIG. 1, a single structure 28, referred to as the interferometer/detector module, provides an interferometer region 30 and a detector region 32. These regions could be provided as separate modules.

In the illustrated interferometer, which has been shown in several earlier patents and applications, light from source 20 is caused by a reflector 34 to direct a collimated beam 36 toward a beamsplitter coating 38 on one side of a stationary wedge-shaped prism 40. The transmitted portion 42 of the beam is one "arm" of the interferometer, and is reflected back on itself by a stationary retroreflector 44. The reflected portion 46 of the beam is the other "arm" of the interferometer, and is reflected back on itself by a stationary retroreflector 48.

A movable wedge-shaped prism 50 is caused to move between its solid line and dashed line positions, in order to provide the spectral scanning function of the interferometer. This type of scanning, which is referred to as refractive scanning, could be replaced by scanning using a moving mirror (flat mirror or retroreflector) without affecting the relevance of the present invention.

FIG. 1, as an example of the possibilities, combines six different sampling peripherals with the basic modular interferometer/detector unit just described.

A multibeam sample compartment 52 is shown, which is arranged to provide several choices for the operator. A collimated beam 54 enters compartment 52 from the interferometer compartment. A parabolic reflector, or parabolic segment 56 is mounted on a rotating assembly, or beam selection wheel (not shown). In one position reflector 56 intercepts beam 54; in another position, it does not, thereby permitting collimated beam 54 to reach a stationary parabolic reflector 58.

If beam 54 is reflected from paraboloid 56, it is caused to exit from the right side of compartment 52, focusing at point 60, and then diverging until it reaches a parabolic reflector 62. The paraboloids 56 and 62 are confocal, and the radiation path between them is enclosed in a modular connecting tube, or arm section, 64. The reflector 62 is itself enclosed in a modular "switching" chamber 65. The term "confocal" indicates that the two parabolic reflectors have a common focal point; it does not require that they have the same focal lengths.

If paraboloid 56 is in the position in which it does not reflect beam 54, the collimated beam is reflected by paraboloid 58, focusing at point 66, and then diverging until it reaches a stationary confocal parabolic reflector 68, which provides collimated beam 70.

In certain usages, the sample which is illuminated will be at point 66. Then post-illumination beam 70 will return directly to the detector compartment 32, in which it is shown reflected by a flat mirror 72. In such situations, a movable parabolic reflector 74, which is shown in the path of beam 70, will have been moved out of the way of that beam.

With the reflector 56 in the position shown, the scanned interferometer output beam will reach movable paraboloid 62, which, depending on its rotational position, will either direct a collimated beam 76 from the solid line position of reflector 62 toward a parabolic reflector 78, or direct a collimated beam 80 from the dashed line position of reflector 62 toward a diffuse reflectance sampler 82. The paraboloid 78 is shown as part of the optical system of a microscope 84.

Paraboloid 78 may, as shown, be movable along a translatory path. In one position (not shown), it allows collimated beam 76 to illuminate microscope 84. In the position shown, it causes the radiation to focus at point 86 inside a modular connecting tube, or arm section, 88. After focusing, the beam diverges until it is reflected by a parabolic reflector 90, which is movable inside a modular "switching" chamber 91. Reflector 90 is movable between its solid line and dashed line positions. In the former position it directs a collimated beam 92 toward a flat 45-degree mirror 94, which reflects the beam into a photoacoustic cell 96. In the latter position, it directs a collimated beam 98 toward a flat 45-degree mirror 100, which is integral to a GC/IR (gas chromatograph infrared) interface 102 (having access to a gas chromatograph 104). Flat mirror 94 is mounted inside a modular chamber 95.

If paraboloid 56 is so positioned as to permit collimated beam 54 to reach paraboloid 58, and if paraboloid 74 is in the position shown, collimated beam 70 will be reflected by paraboloid 74 to a focal point 104. The focused beam, which is enclosed by a modular connecting tube, or arm section, 106, then diverges until it is reflected by a parabolic reflector 108. This reflector has two available positions. In its solid line position, it reflects a collimated beam 110, which passes through a modular connecting tube 112 into an automatic sample profiler 114. In its dashed line position, paraboloid 108 reflects a collimated beam 116 into a horizontal access ATR (attenuated total reflectance) sampler 118. The reflector 108 is itself enclosed in a modular "switching" chamber 120.

Inside ATR 118, a pair of confocal parabolic reflectors 122 and 124 cause illumination in a sample container 126. A collimated beam 128 leaving paraboloid 124 passes through a modular connecting tube 130 into a modular "switching" chamber 132, in which a movable flat mirror 134 is mounted. In its dashed line position, mirror 134 directs the radiation from ATR 118 toward a detector module 136.

Inside sample profiler 114, a pair of confocal parabolic reflectors 138 and 140 cause illumination of a sample at 142. A collimated beam 144 leaving paraboloid 140 is reflected by the flat mirror 134, in its solid line position, toward detector module 136.

Each modular unit in the system, including members 52, 64, 65, 82, 84, 88, 91, 95, 96, 102, 106, 112, 114, 118, 120, 130 and 132, has precisely dimensioned flanges at its inlet and outlet openings, each of which flanges engages, and is secured to, a matching flange on the adjacent modular unit. These flanges, when secured together, ensure proper alignment of the optical components in one unit with those in the other units.

It will be apparent, from the foregoing description of an example of a possible combination of modular units, that the operator's experiments can be greatly simplified and accelerated by the ready accessibility of pre-installed sample-analyzing units. While the system can be readily rearranged, if necessary, the possibility of having multiple sample-analyzing units simultaneously in place offers obvious savings in time and effort.

The system of the present application emphasizes modularity, which both (a) simplifies changing the units included in the system, and (b) substantially reduces costs by maximizing the use of interchangeable parts. In other words, the system can be readily set up and changed with the "building blocks" provided.

Broadly, the units may be divided into three general categories. The first category includes the modular interferometer/detector unit 28, and the modular sample units 52, 82, 84, 96, 102, 114 and 118. The second category includes the radiation reflecting modules 65, 91, 95, 120 and 132. These radiation reflecting modules may contain parabolic reflectors or planar (flat) reflectors; the positions of their reflectors may be movable or stationary. Also, several of the accessory modules contain movable reflectors. The third category includes the modular connecting tubes 64, 88, 106, 112 and 130.

Figure 2:
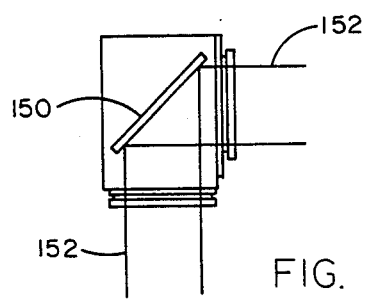
FIGS. 2-8, which correspond, respectively, to FIGS. 5-11 of Ser. No. 895,211 (except for the reference numerals), show schematically seven different modular units containing planar or parabolic mirrors.
Figure 3:
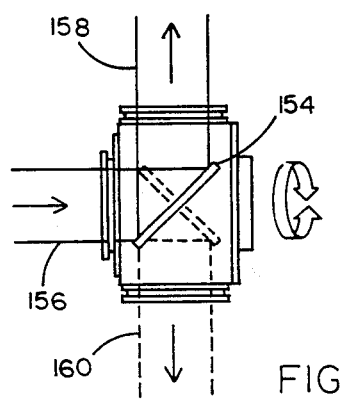

FIGS. 2-8 show schematically seven basic versions of the modular radiation reflecting units. FIG. 2 shows a modular unit having a fixed planar mirror 150, which reflects a collimated beam 152 to change its direction. FIG. 3 shows a modular unit having a planar mirror 154 whose position is rotatable around a vertical axis to direct an incoming collimated beam 156 either in the direction of beam 158 (solid line position) or in the direction of beam 160 (dashed line position).

Figure 4:
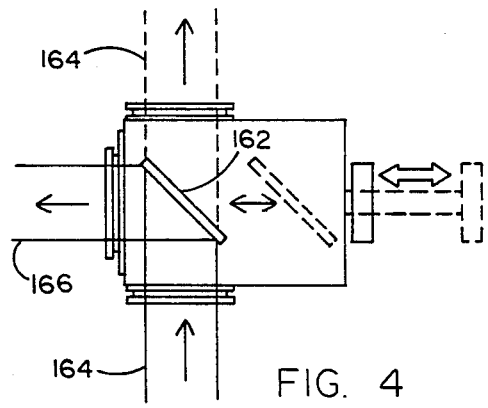

FIG. 4 shows a modular unit having a planar mirror 162 whose position is translational between its solid line position, in which it reflects beam 164 to provide beam 166, and its dashed line position, in which it does not reflect beam 164, permitting the beam to go directly through the modular unit.

Figure 5:
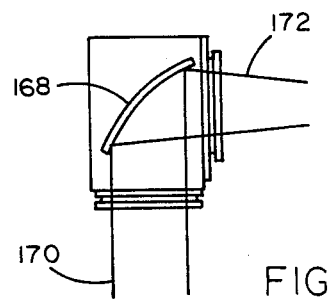

FIGS. 5-8 show different modular units containing parabolic reflectors, which both change the direction of the radiation beam, and change its nature from a collimated beam to a focused beam, and vice versa. In FIG. 5, a fixed parabolic reflector 168 is shown, which can input collimated beam 170 and output (converging) focused beam 172, or input focused (diverging) beam 172 and output collimated beam 170.

Figure 6:
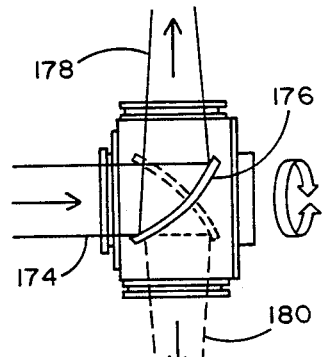
Figure 7:
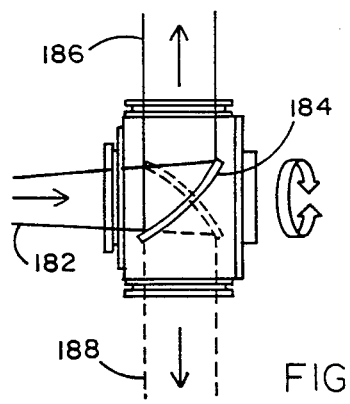

FIGS. 6 and 7 show two modular "switchable" units, each of which has a rotary parabolic reflector capable of directing the output beam in either of two directions. In FIG. 6, the input beam is a collimated beam 174, which is reflected by a parabolic mirror 176. The beam is converted into a converging beam 178 in one direction when mirror 176 is in its solid line position, and is converted into a converging beam 180 in the opposite direction when mirror 176 is in its dashed line position. In FIG. 7, the input beam is a diverging beam 182, which is reflected by a parabolic mirror 184. The beam is converted into a collimated beam 186 in one direction when mirror 184 is in its solid line position, and is converted into a collimated beam 188 in the opposite direction when mirror 184 is in its dashed line position.

Figure 8:
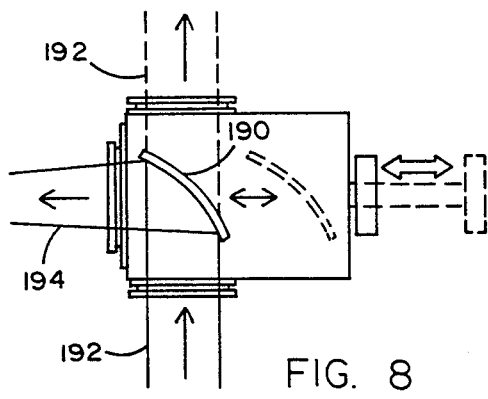

FIG. 8 shows a modular unit having a parabolic mirror 190 whose position is translational between its dashed line position, in which a collimated beam 192 goes directly through the modular unit, and its solid line position, in which collimated beam 192 is reflected by mirror 190 to output a converging beam 194.

Figure 9:
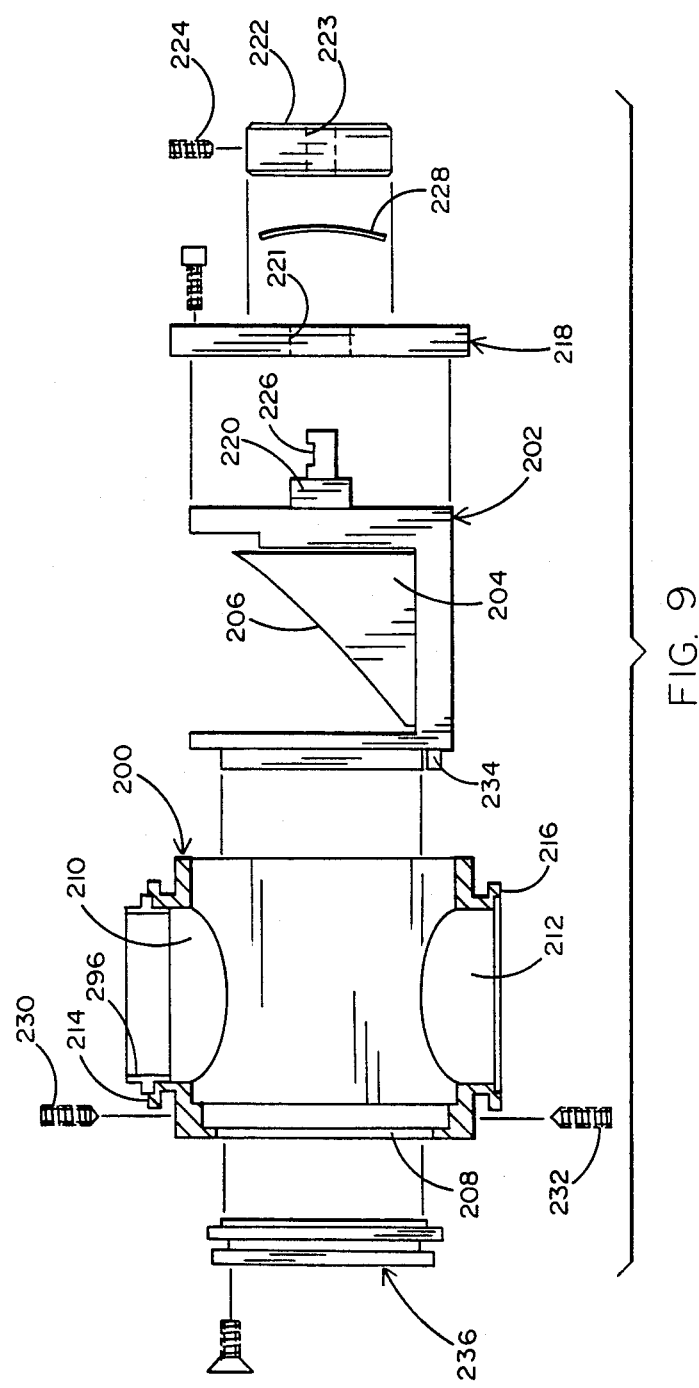
FIG. 9 is an exploded view showing an optical "switch" component of the system.

FIG. 9 is an exploded view of one of the most important and versatile of the modular building blocks. It is an optical "switch" assembly, the term "switch" indicating that the optical reflecting element is movable to change the direction, or form, of the radiation beam. The optical element in FIG. 9 may be rotated about its optical axis to change the direction of the exiting radiation beam.

A switch body 200 is designed to contain a rotary mirror mount assembly 202, which has secured thereto a mirror body 204 having a reflecting surface 206. In FIG. 9, the reflecting surface 206 is parabolic, but a mirror having a flat reflecting surface could be secured to the same mirror mount assembly 202.

As shown in FIG. 9, switch body 200, which is shown in horizontal cross-section, has openings on three sides—208, 210 and 212, through which the radiation beam may pass. If desired, fourth and even fifth openings could be provided in the top and bottom of switch body 200.

The rotation of rotary mirror mount 202 must occur around the axis of symmetry of the radiation beam. This axis may be defined as the line followed by the central ray in the collimated beam. With a parabolic mirror, one beam (entering or exiting the switch body) will be collimated and the other will be focused (diverging or converging). The same center ray which travels along the center of the collimated beam also travels along the center of the converging or diverging beam.

Thus, both collimated and focusing beams have axes of symmetry. And these axes of symmetry provide two constraints in designing the modular components of the present system. The axis of rotation of the rotary mirror mount 202 should be colinear with the axis of symmetry of the beam passing through opening 208. And the axes of symmetry of the beams passing through openings 210 and 212 should be perpendicular to their respective mating flange surfaces 214 and 216, a subject which will be discussed in greater detail below.

The axis of rotation of the parabolic reflector is colinear with the axis of symmetry of the reflected beam, but not with the axis of symmetry of the parabola (of which the reflector is a parabolic segment). In the case in which the reflector is rotated around the axis of symmetry of a collimated beam, the axis of symmetry of the parabola is parallel to, but not co-linear with, the axis of symmetry of the beam. In the case in which the reflector is rotated around the axis of symmetry of a focused beam, the axis of symmetry of the parabola is perpendicular to the axis of symmetry of the beam.

After rotary mirror mount 202 has been inserted in switch body 200, it is held in place by a cover 218, which is secured to the right side of the switch body. A circular shaft 220, integral with mirror mount 202, extends through an opening 221 in cover 218. A knob 222 has an opening 223, which receives the end of shaft 220, and is secured to it by a set screw 224 engaging a flat 226 on the flange. A spring washer 228 is mounted between knob 222 and cover 218, for the purpose of exerting a resilient force holding the rotary mirror mount 202 in frictional engagement with cover 218, thus avoiding undesired movement of the mirror mount 200 after it has been rotated to its desired position.

Two stops are provided, each of which blocks rotation of the mirror mount 202 after it has been rotated either clockwise or counter-clockwise to reach one of its two operating positions. Each of the stop positions may be adjustably determined by one of two cone point set screws 230 and 232, each of which is screwed into the switch body 200. In other words, each set screw 230 and 232 may be initially moved by threaded adjustment into its exact position for proper mirror alignment. A bar magnet 234 is secured to the rotary mount 202, and engages the appropriate screw 230 or 232. The purpose of the magnet 234 is to provide a force holding the interengaging stop members together after rotation of the mirror mount from one position to the other.

An interface element 236 is secured to the left side of the switch body 200. The structures of (a) this element (which is a frequently used component of the modular system), (b) the switch body 200, and (c) the cover 218, are shown in greater detail in FIGS. 10-14. The outer end of interface element 236 is shown in FIG. 10, and its cross-section is shown in FIG. 11. As seen in FIG. 10, the interface element has an annular portion 237 having an annular recess 238, a round opening 240, and a square peripheral flange 242, by means of which it is secured to the side of switch body 200.

FIGS. 12 and 13 show, in vertical elevation, the left end and right end, respectively, of switch body 200. The flat peripheral flange 242 of interface element 236 is secured against a similarly shaped flat end surface 244 at one end of switch body 200, by means of suitable threaded fasteners (four threaded openings are shown).

FIG. 12a is an enlarged view showing the bar magnet 234 in engagement with the conical inner end of one of the set screws 230/232.

FIG. 14 is an elevation showing cover 218, which is square in shape, and is secured against a peripheral flange of a flat end surface 246 (FIG. 13) of switch body 200, by means of suitable threaded fasteners (four threaded openings are shown). A centrally located round opening 221 is provided for shaft 220.

Figure 16:
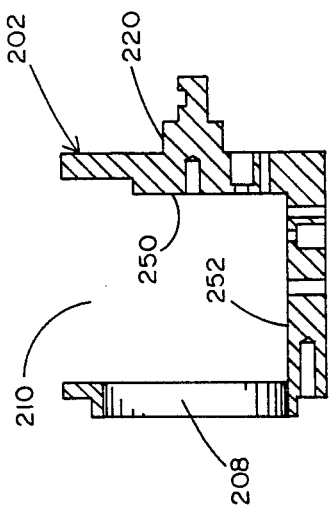
FIGS. 15 and 16 are, respectively, an end view in elevation, and a horizontal cross-section, showing the rotary mount which carries the mirror in the optical switch.
Figure 15:
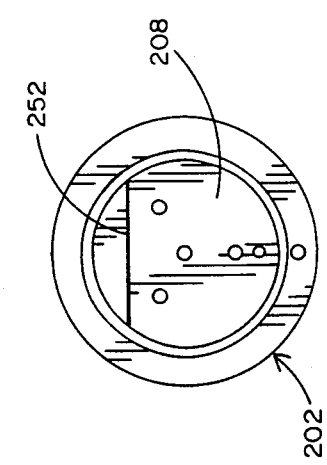

The rotary mount 202, which is essentially cylindrical in form, and which is rotatably mounted inside switch body 200, is shown in greater detail in FIGS. 15—18. FIGS. 15 and 16, respectively, are an end view in elevation, and a horizontal cross-section, showing the rotary mount, which carries the mirror (parabolic or flat). Openings 208 and 210 are visible in these figures. Rotation of the mount 202 is caused by rotation of shaft 220, which extends from a side wall having a flat vertical inner surface 250. Surface 250 is perpendicular to the axis of symmetry of the radiation passing through opening 208, and is in a plane parallel to the axis of symmetry of the radiation passing through opening 210 (and opening 212, which is not shown in FIG. 16). A flat horizontal inner surface 252 is provided inside the cylindrical portion of rotary mount 202, which is adapted to support a parabolic mirror in certain situations. Surface 252 is in a plane parallel to the of axis symmetry of radiation passing through opening 208, and is perpendicular to the axis of symmetry of radiation passing either through opening 210 or through opening 212.

Figure 18:
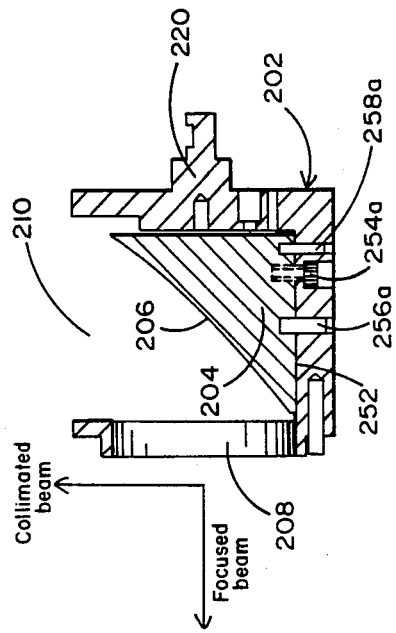
FIGS. 17 and 18 illustrate two different positions in which the mirror of the optical switch may be secured to its rotary mount.
Figure 17:
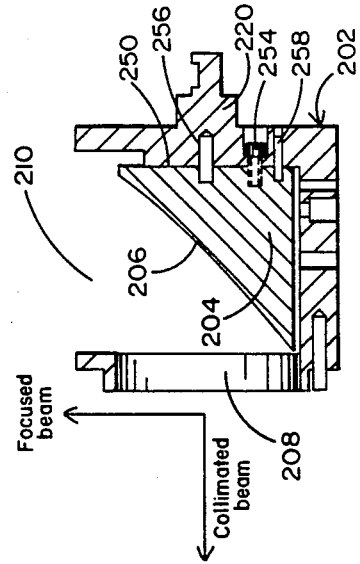

FIGS. 17 and 18 illustrate that the rotary mount 202 and mirror body 204 (having reflecting surface 206) are capable of being repositioned with respect to one another, in order to accommodate either a collimated or a focused beam at opening 208, combined with the other beam type at openings 210 and 212. This is not a change which can be made by the operator after the system is set up; but it provides a choice during initial assembling or re-assembling of the switch body 200. Because the same parts are used in either arrangement, parts inventory requirements are reduced.

FIG. 17 shows mirror body 204 so mounted that its surface 206 reflects a focused beam through opening 210 and a collimated beam through opening 208. In this position the mirror body is secured against surface 250 by a plurality of screws 254, after being accurately positioned by aligned dowel pins 256 and 258.

FIG. 18 shows mirror body 204 so mounted that its surface 206 reflects a collimated beam through opening 210 and a focused beam through opening 208. In this position the mirror body is secured against surface 252 by a plurality of screws 254a, after being accurately positioned by aligned dowel pins 256a and 258a.

In both FIGS. 17 and 18, rotation of mirror mount 204 to accomplish beam switching is caused by rotation of shaft 220. And in both figures, the axis of rotation of the mirror is colinear with the axis of symmetry of the incoming beam.

Figure 19:
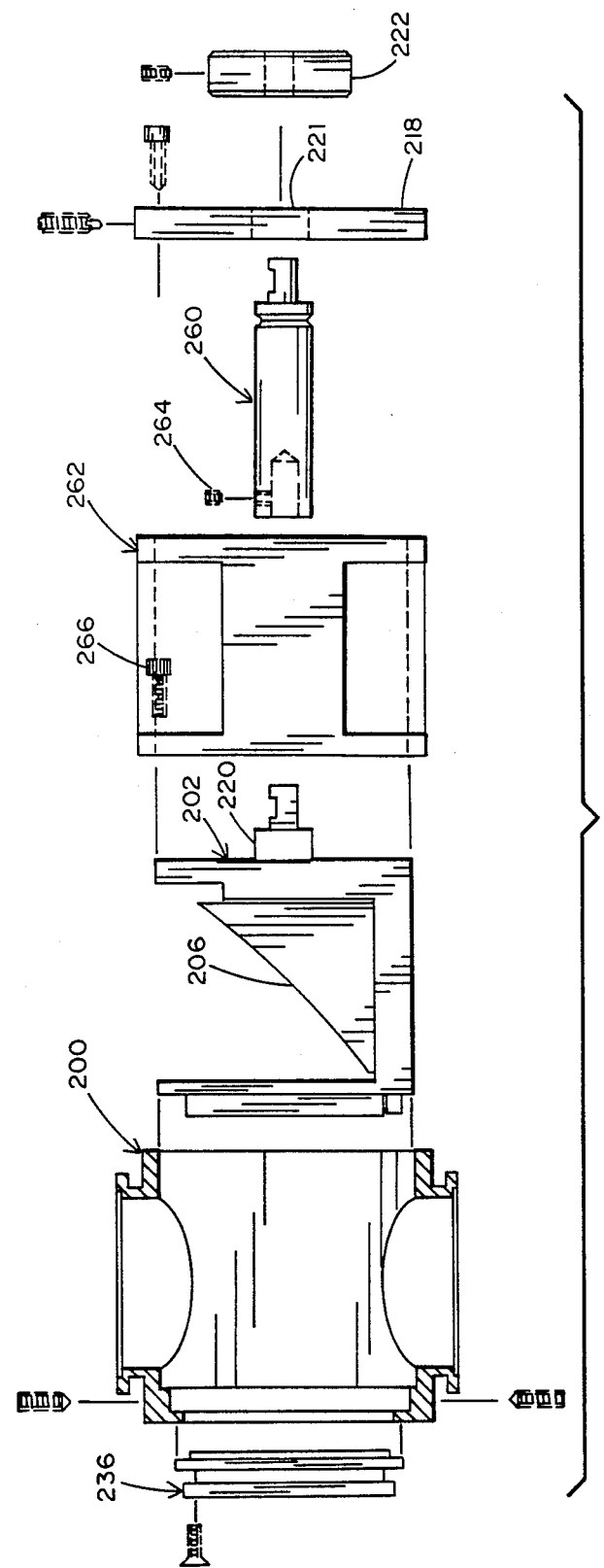
FIG. 19 is an exploded view similar to FIG. 9, except that it provides for translatory movement, as well as rotary movement, of the switchable mirror.

FIG. 19 is an exploded view similar to FIG. 9, except that it provides an even more versatile modular component because it includes, as an added feature, extension parts which permit the mirror mount to be moved out of the path of the radiation. The parts which are common to the two figures have the same reference numerals as in FIG. 9, e.g., switch body 200, rotary mirror mount 202, cover 218, shaft 220, knob 222, and interface element 236.

In order to cause translational movement of mirror mount 202, in FIG. 18 a shaft extension 260 and a switch body extension 262 are added to the elements in FIG. 9. The shaft extension 260 is secured to shaft 220 by a set screw 264. The switch body extension 262 is secured to the flange at the right side of switch body 200 by means of a plurality of threaded fasteners 266.

When the operator desires to remove mirror surface 206 from the radiation path, thereby permitting radiation passthrough, knob 222 is pulled to the right. Mirror mount 202 moves to the right into body extension 262, where it does not reflect the radiation beam. In this situation, the switch body 200 is merely a pass-through for the radiation.

FIGS. 20 and 21 are, respectively, an exploded view of a modular connecting tube assembly, and an end view of the connecting tube. Square cross-section tubes 270 may be used for interconnection of the optical components. The connecting tubes are available in various lengths. As a convenience, separate interface elements 236a and 236b may be secured to opposite ends of tube 270 by means of fasteners 272 threaded into openings 274 in the ends of the tube. The interface elements 236 are standard parts, which preferably are available in at least two versions, one relatively thin, and one somewhat thicker. Those shown in FIG. 20 have the thinner dimensions.

The modular connecting tubes 270 prevent ambient radiation from reaching the analytical radiation in the system. They also provide an enclosure, which can maintain a "purged" environment, i.e., one in which an inert gas, such as nitrogen, replaces the ambient atmosphere. A purged environment in the system may be maintained by continually pumping the purging gas in at one end, e.g., the spectrometer unit, and letting it leak through the other end, or ends, of the system; or by providing purge inlets at various points in the system, such as one in each tube section.

FIGS. 22-24 are, respectively, a cross-section, and two end views of an interface element 236c having the thicker dimension. The interface elements 236 each have a cylindrical central aperture 276, and a square-shaped peripheral flange 278 adapted to be secured to an adjacent element, by means of fasteners in openings 280. Flange 278 may be secured to any modular component, such as the tube 270 of FIGS. 20 and 21, or the switch body 200 of FIGS. 9 and 19.

The interface elements 236 are used to ensure correct alignment of adjacent modular components in the system. It is much easier, and thus less expensive, to hold manufacturing tolerances on the small interface elements than on the much larger components which are interconnected by the interface elements.

For practical reasons, each engaging flange of each component and of each interface element needs to be machined to provide a flat surface to which the axis of the radiation beam is perpendicular. Also, adjacent components in the system should be so aligned that the radiation beams are essentially centered in the pass-through apertures and tubes. This combination of manufacturing constraints ensures correct alignment of the optical system, regardless of the configuration in which the modular components are set up for convenient operation.

As seen in FIGS. 22 and 24, the right end 286 of the interface element has a cylindrical center bore, but a noncylindrical periphery 288 which fits inside a similarly shaped recess in the adjacent modular component (and thus prevents relative rotation of the modular component and the interface element). As seen in FIGS. 22 and 23, the left end 290 of the interface element has an annular peripheral interface flange 292, and an annular recess 294 inside flange 292. The purpose of recess 294 is to receive a centering ring, which is inserted into recesses in two adjacent interface elements, in order to ensure their alignment (while permitting relative rotation of the engaging interface elements to any desired position).

FIGS. 25 and 26 are side and end views, respectively, of a centering ring 296. The centering ring has an annular peripheral flange 298 which fits into the recesses 294 of two adjacent interface elements to align those elements. The smaller diameter annular sides 300 and 302 of centering ring 296 extend inside the cylindrical apertures 276 of the two engaging interface elements. In order to keep the centering ring from falling out of place during assembly, each annular side 300 and 302 may have a plurality of deformable plastic ribs 304 on its outer surface to engage the inner peripheries of apertures 276 in the respective interface elements.

When the two adjacent interface elements and the centering ring have been assembled, an outer clamp (not shown) may be tightened to hold the assembled elements in position.

Because the flat engaging surfaces of the interface elements ensure beam perpendicularity, and the centering ring ensures alignment of their apertures, the interface elements may be rotated with respect to one another, without losing alignment in the system. If two optical components need to be located at vertically different levels, this can be easily provided by relative rotation of the interengaging interface elements, whose axes of rotation are fixed by the centering rings between each pair of interengaging interface elements.

FIG. 27 is an exploded view showing a corner tube assembly 305, which is used to provide right angle reflection of a radiation beam. The corner tube assembly includes a tube 270a, which is similar to, but shorter than, the tube in FIG. 20. At a first side 306 of tube 270a, it is engaged by, and secured to, a thin interface element 236d. At a second side 308 of tube 270a, which is in a plane perpendicular to side 306, the tube is engaged by, and secured to, a thick interface element 236e. At a third side 310 of tube 270a, which is opposite side 306, the tube is engaged by, and secured to, a mirror end mount assembly 312, which carries a mirror having a reflecting surface 314. The mirror may be selected from a group of available types, including a flat mirror and a plurality of parabolic mirrors having different focal lengths.

As is apparent from the foregoing description, the benefits of modularity have been provided both by the use of modular sub-assembly components in the system, and by the use of modular parts in the components.

Figure 28:
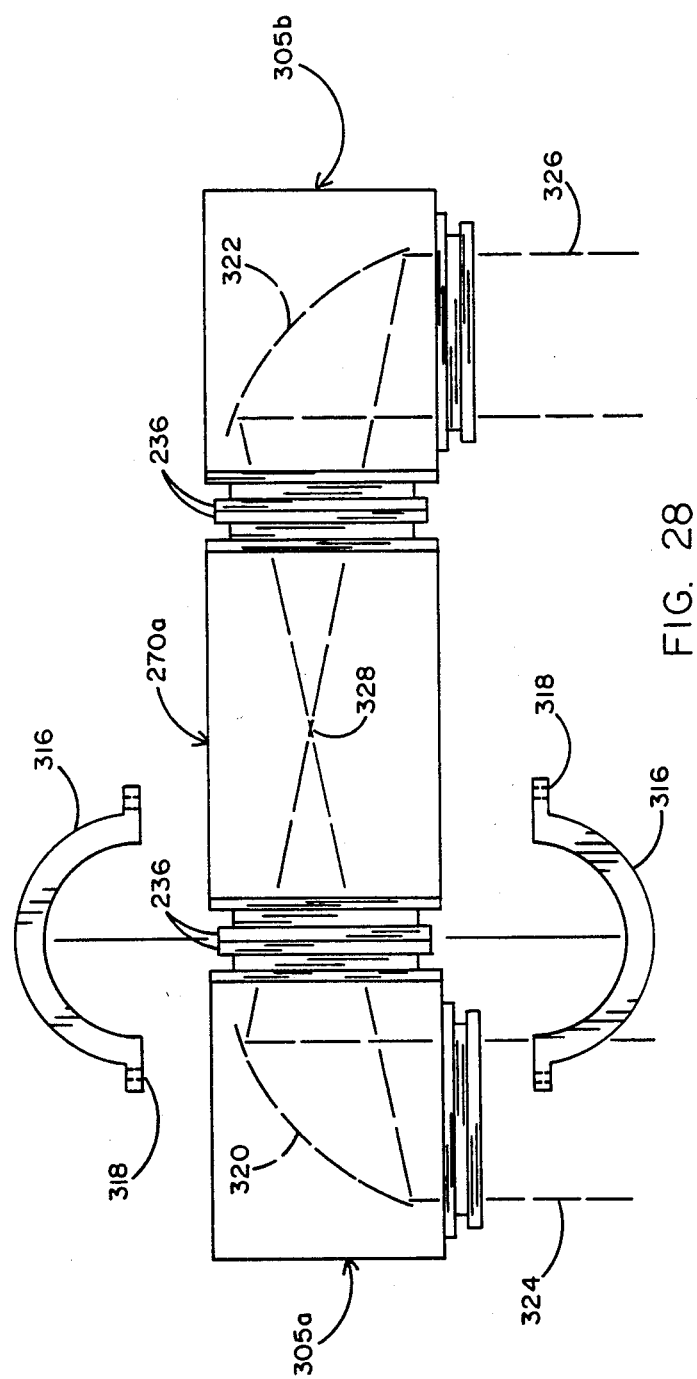
FIG. 28 shows a sub-system incorporating a plurality of modular elements and units previously described individually.

FIG. 28 illustrates another sub-system demonstrating the benefits of this comprehensive design modularity. In related application (Ser. No. 895,211), one of the important concepts is the use of two confocal parabolic mirrors to reimage a collimated entering beam, in order to avoid vignetting in the system. In FIG. 28, such a confocal segment of the system is provided, using modular elements already described.

A connecting tube 270a (see FIG. 20) is interposed between, and connected to, two corner tube assemblies 305a and 305b (see FIG. 27). The interconnection at each end of tube 270 is provided by a pair of interface elements 236 (see FIGS. 20-24). Each pair of interface elements has an internal centering ring (not seen in FIG. 28), and an external clamping means, provided by a pair of U-shaped metal brackets 316, having flanges 318 which are brought together by threaded parts, in the customary manner.

A parabolic reflector 320 is mounted inside corner tube assembly 305a, and a parabolic reflector 322 is mounted inside corner tube assembly 305b. Collimated beams 324 and 326 are caused to focus at 328 by the confocal parabolic mirrors. Because the centering rings ensure that any relative rotation of the interface elements 236 will occur around the axis of the radiation beam, relative rotation between components of the system can be made, in order to accommodate location adjustments, without disturbing the optical alignment of the system. Thus, adjustments can easily be made to permit interconnected parts of the system to extend at various angles, and to be supported on various levels.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. An interferometer spectrometer system which includes a radiation source, one or more detector components, an interferometer outputting a radiation beam, and a modular optical switching component comprising:

a housing having a first aperture through which a radiation beam may pass, and second and third apertures through which that radiation beam may also pass;

the arrangement being such that the radiation beam axis of symmetry through the first aperture makes the same angle with the radiation beam axis of symmetry through the second aperture as it does with the radiation beam axis of symmetry through the third aperture;

means for mechanically connecting the housing to at least two other components in the system, in such a way that the system may be readily rearranged by detaching the housing from one system component and attaching it to another system component;

a mirror-supporting member rotatably mounted in the housing, the axis of rotation of such member being colinear with the axis of symmetry of the beam passing through the first aperture;

a reflecting surface which is carried by the mirror supporting member and which is designed to reflect a beam entering the first aperture through either the second or third aperture, or to reflect a beam entering either the second or third aperture through the first aperture;

means for turning the mirror-supporting member on its axis to select either a position in which the radiation travels through the second aperture, or a position in which the radiation travels through the third aperture; and means for releasably retaining the mirror-supporting member in its selected position.

2. The interferometer spectrometer system of claim 1 in which the radiation beam axis of symmetry through the first aperture is perpendicular to the radiation beam axes of symmetry through the second and third apertures.

3. The interferometer spectrometer system of claim 1 in which the reflecting surface is a parabolic mirror.

4. The interferometer spectrometer system of claim 3 in which the beam traveling through the first aperture is a collimated beam and the beam traveling through the second or third aperture is a focusing beam.

5. The interferometer spectrometer system of claim 3 in which the beam traveling through the first aperture is a focusing beam and the beam traveling through the second or third aperture is a collimated beam.

6. The interferometer spectrometer system of claim 1 in which the housing and the mechanical connecting means provide a continuous enclosure inside which the radiation beam travels along a path the center of which coincides with the center of the enclosure, so that rearrangement of the system does not alter the alignment of the radiation path.

7. The interferometer spectrometer system of claim 6 in which:
the housing and the mechanical connecting means have contacting planar surfaces provided with aligned radiation apertures, such contacting surfaces lying in planes perpendicular to the axis of symmetry of the radiation beam which passes through the aligned apertures.

8. The interferometer spectrometer system of claim 1 which also comprises:
a modular connecting tube through which radiation passes between the housing and other components in the system.

9. An interferometer spectrometer system which includes a radiation source, one or more detector components, an interferometer outputting a radiation beam, one or more optical reflectors, and modular components comprising:
one or more linearly-extending enclosure components having an internal passage inside which the radiation beam travels in a linear direction;
one or more non-linearly-extending enclosure components having an internal passage inside which the direction of the radiation beam is changed by an optical reflector; and
one or more pairs of interface elements which join adjacent enclosure components, and which are readily detachable from such components, in order to permit rearrangement of the components in the spectrometer system;
each element of each pair of interface elements having a first end flange engaging and secured to one of the enclosure components, and a second end flange engaging and secured to the other one of the paired interface elements.

10. The interferometer spectrometer system of claim 9 in which each of the paired interface elements has a central cylindrical internal passage which has an axis of rotation colinear with that of its paired interface element, in order to permit relative rotation of the paired interface elements without changing their alignment.

11. The interferometer spectrometer system of claim 10 in which the colinear axes of rotation of the paired interface elements permit their relative rotation without changing the angle between the axis of such rotation and the surface of an optical reflector which receives radiation traveling through the interface elements.

12. The interferometer spectrometer system of claim 11 which also comprises:
a centering ring internally engaging both of the paired interface elements for the purpose of maintaining their alignment while permitting their relative rotation around their colinear axes; and
clamping means externally engaging both of the paired interface elements to secure them in their selected relative positions.

13. The interferometer spectrometer system of claim 9 wherein the non-linearly extending enclosure component or element component contain:
a mirror which reflects radiation traveling in one direction in such a way as to provide radiation traveling in another direction perpendicular to the former direction.

14. The interferometer spectrometer system of claim 12 wherein the non-linearly extending enclosure component or components contain:
a mirror which reflects radiation traveling in one direction in such a way as to provide radiation traveling in another direction perpendicular to the former direction.

15. The interferometer spectrometer system of claim 13 in which the mirror is a parabolic mirror which reflects a collimated beam in one direction so as to form a focusing beam in the other direction, or vice versa, the axes of symmetry of the beams being at right angles to one another.

16. The interferometer spectrometer system of claim 14 in which the mirror is a parabolic mirror which reflects a collimated beam in one direction so as to form a focusing beam in the other direction, or vice versa, the axes of symmetry of the beams being at right angles to one another.

17. An interferometer spectrometer system which includes a radiation source, a detector, an interferometer outputting a radiation beam, one or more optical reflectors, and modular components comprising:
one or more linearly-extending enclosure units having an internal passage inside which the radiation beam travels in a linear direction;
one or more non-linearly-extending enclosure units having an internal passage inside which the direction of the radiation beam is changed by an optical reflector;
each enclosure unit having at one end thereof a cylindrical aperture and a planar surface surrounding such aperture, each aperture having an annular recess formed therein;
the axis of symmetry of each radiation beam in the system being perpendicular to the planar surface through which the beam passes;
means for interconnecting two of the enclosure units in such a way that they may be readily disconnected and reconnected, in order to permit rearrangement of the enclosure units in the system; and
a centering ring extending into and engaging the walls of the annular recesses in the two interconnected enclosure units.

18. In an interferometer spectrometer system which includes a radiation source, a detector, and an interferometer outputting a radiation beam, a modular sub-system comprising:
a first sample-enclosing housing adapted to apply post interferometer radiation to analysis of a sample in a desired mode;

a second sample-enclosing housing adapted to apply post interferometer radiation to analysis of a sample in a desired mode;

means for mechanically interconnecting the first and second sample-enclosing housings, in such a way that the system may be readily rearranged by disconnecting either housing from the system;

a movable parabolic reflector which has an input radiation beam received directly or indirectly from the interferometer, and an output beam which is adapted to travel toward either the first or second sample-enclosing housing depending on the position of the movable reflector; and rotating means for moving the reflector around an axis which is co-linear with the axis of symmetry of the input beam received by the reflector.

19. The modular sub-system of claim 18 in which:

the input radiation beam received by the reflector is a collimated beam; and the rotating means moves the reflector around an axis of rotation which is parallel to, but displaced laterally from, the axis of symmetry of the parabola, in order to switch the location of the focus of the reflector from one position to another.

20. The modular sub-system of claim 18 in which:

the input radiation beam received by the reflector is a focusing beam; and the rotating means moves the reflector around an axis of rotation which is perpendicular to the axis of symmetry of the parabola and which passes through the focus of the parabola, in order to switch the collimated output beam of the reflector from one position to another.

21. In an interferometer spectrometer system which includes a radiation source, a detector, and an interferometer outputting a radiation beam, a modular sub-system comprising:

a first modular unit having a cylindrical aperture surrounded by a planar surface, the aperture being provided for the entry or exit of a radiation beam whose axis of symmetry is centered in the cylindrical aperture and is perpendicular to the planar surface;

a second modular unit having a cylindrical aperture surrounded by a planar surface, the aperture being provided for the entry or exit of a radiation beam whose axis of symmetry is centered in the cylindrical aperture and is perpendicular to the planar surface;

the first and second modular units having their planar surfaces in engagement with one another, and being mechanically interconnected in such a way that the system may be readily rearranged by detaching them from one another;

each of the first and second modular units having an annular recess formed in its cylindrical aperture at its planar surface; and a centering ring extending into and engaging the walls of the annular recesses in the respective modular units, in order to ensure centerality of the axis of symmetry of the radiation beam, while permitting relative rotation of the first and second modular units.

* * * * *